United States Patent [19]

Wright et al.

[11] Patent Number: 5,087,716

[45] Date of Patent: Feb. 11, 1992

[54] SYNTHESIS OF DIFUNCTIONAL HALO ORGANO NONCARBON GROUP IV MAIN GROUP ELEMENT AMIDES

[75] Inventors: Antony P. Wright, Rhodes; Padmakumari J. Varaprath, Midland, both of Mich.

[73] Assignee: Dow Corning Corporation, Midland, Mich.

[21] Appl. No.: 607,194

[22] Filed: Dec. 24, 1990

Related U.S. Application Data

[62] Division of Ser. No. 467,868, Jan. 22, 1990.

[51] Int. Cl.$^5$ ............ C07F 7/10; C07F 7/22; C07F 7/24
[52] U.S. Cl. ............ 556/413; 556/87; 556/417; 556/423; 556/425; 556/478; 556/482; 556/484; 556/487
[58] Field of Search ............ 556/407, 410, 411, 413, 556/417, 418, 478, 423, 400, 425, 482, 484, 87, 487

[56] References Cited

U.S. PATENT DOCUMENTS 3,146,250 8/1964 Speier ............ 260/448.2
4,608,270 8/1986 Varaprath ............ 427/35

FOREIGN PATENT DOCUMENTS 3902483 9/1989 Fed. Rep. of Germany ...... 556/425

Primary Examiner—Jose G. Dees
Assistant Examiner—Porfirio Nazario
Attorney, Agent, or Firm—George A. Grindahl

[57] ABSTRACT

Difunctional halo silicon amide compounds are prepared by cleaving the nitrogen-silicon bond in a nitrogen-silicon heterocycle with a reactive halide. The reaction is straight forward with no intermediates or by-products. The halo functionality is capable of capping any SiOH group. When the other functionality is an acrylamide, the capped entity may be polymerized or crosslinked by free radical initiators of the acrylamide functionality thereby producing useful products such as paper release coatings and photoresists.

15 Claims, No Drawings

SYNTHESIS OF DIFUNCTIONAL HALO ORGANO NONCARBON GROUP IV MAIN GROUP ELEMENT AMIDES

This is a continuation of copending application Ser. No. 07/467,868 filed on Jan. 22, 1990, allowed.

BACKGROUND OF THE INVENTION

This invention relates generally to a method for preparing noncarbon Group IV main group element compounds that contain two reactive sites. More specifically, the method involves cleavage of a cyclic noncarbon Group IV main group element-nitrogen bond with a reactive halide moiety to yield reactive halo and amide functional groups in the same molecule The pursuit of a synthetic pathway for incorporating free radical curable functionality onto the siloxane backbone has been long and difficult. For example, it is noted that organosilicon compounds that contain silicon-bonded acylamino-substituted hydrocarbon radicals are known and have been described in publications such as U.S. Pat. No. 4,608,270 to I5 Varaprath, which is herein incorporated by reference. As noted in Varaprath U.S. Pat. No. 4,608,270 and as taught in U.S. Pat. No. 2,929,829 to Morehouse, Japan 51/108022 to Furuya et al., Japan 56/74113 to Takamizawa, and West German DE 2365272 to Koetzsch et al., acylaminoorganopolysiloxanes can be synthesized by reacting aminosiloxanes with the corresponding acid chloride in the presence of a tertiary amine such as triethylamine. Such a synthesis has several disadvantages. First, the removal of the voluminous precipitate of triethylamine hydrochloride by filtration is tedious. Second, even when an excess of amine is used, a small amount of HCl is liberated that is detrimental to the stability of the polymer, especially when the acid chloride has other reactive vinyl functionality such as where the acid chloride is methacrylyl chloride.

An alternative method for the preparation for the acylaminoorganopolysiloxanes involves the reaction of aminosiloxanes and silanes with an acid anhydride or ester at elevated temperature. This is taught in U.S. Pat. No. 4,507,455 to Tangney and Ziemelis, assigned to the assignee of the present invention. Unfortunately at the elevated temperatures of the reaction, acrylamide derivatives undergo Michael addition and amidation of the acrylic double bond, resulting in unwanted by-products and crosslinkage of the desired product which ultimately causes the polymer to gel.

As taught in the above-mentioned U.S. Pat. No. 4,608,270 to Varaprath, these problems can be overcome by reacting the aminosilanes and siloxanes with acid chlorides in the presence of aqueous sodium hydroxide. The HCl that is produced on addition of acyl chloride is neutralized by hydroxide in the aqueous phase. However, a problem arises from the fact that this reaction is carried out in a two-phase system in which the aminosiloxane is dissolved in an organic solvent that is immiscible with water. Because the amide function is generally highly polar and hydrophilic, it has a tendency to absorb moisture. Incorporation of these units into the siloxane backbone increases water miscibility causing the polymers to emulsify easily thus making phase separation difficult.

To some extent, this problem can be overcome by using chlorinated solvents such as methylene chloride or chloroform but, unfortunately, such solvents are toxic. Moreover, when larger amounts of amide functionality or a more resinous structure or both are used, it is almost impossible to prepare such compounds using a two-phase system even when chlorinated solvents are used.

Accordingly, a need remains for an improved method for preparing organosilicon amide compounds that avoids the phase separation and solvent toxicity problems previously encountered.

A need remains for an expanded method that permits use of silane starting materials having hydrolytically unstable groups such as Si—O—CH$_3$. A need remains for an improved method of preparing organosilicon amide compounds that minimizes the production of by-products that must be phase separated, filtered, and/or washed from the product. A need exists to avoid amine and acrylylamide functionality in the starting materials for preparing siloxane polymers and in the starting siloxane polymer itself. Instead the monomeric acrylylamide functionality should be coupled to the silicon polymer as a concluding step. All of these problems and attendant needs strongly suggest that there is still a need for an easy synthetic pathway to incorporate free radical curable functionalities onto the silioxane backbone.

A method for making nitrogen derivatives of a variety of elements is known:

$$Y_3MNRR' + R''X \rightarrow Y_3MX + R''NRR'$$

where Y is alkyl, aryl, or a halide; M is silicon, germanium, or tin; NRR' is —NRR' (where R and R' are organic radicals), —NCO, NHSi, imidazole, —N=S=N—, —N=CPh$_2$, —N$_3$, —NSO, —N=PR$_3$, —NSO$_2$R, —NPhCSMe, or —NRBEt$_3$; and R"X is acyl halide, alkyl halide, phosgene, PhSO$_2$Cl, SO$_2$Cl$_2$, SOCl$_2$, S$_2$Cl$_2$, ClSO$_2$NCO, RN=SF$_2$, RN=SCl$_2$, R$_2$NSCl, ClSO$_2$NCO, PCl$_3$, OPCl$_3$, PhPOCl$_2$, (Cl$_3$P=N)$_2$SO$_2$, BCl$_3$, PhBCl$_2$, R$_2$BCl, AlCl$_3$, FeCl$_3$, BeCl$_2$, SbCl$_5$, PhN=CCl$_2$,NOCl, PR$_2$F$_3$, R$_2$AsCl, Me$_2$NSOCl, S$_3$N$_2$Cl$_2$, CF$_3$SF$_3$, (ClSO$_2$)$_2$NH, Mn(CO)$_5$Br, Mo(C$_5$H$_5$)(CO)$_3$Cl, W(C$_5$H$_5$)(CO)$_3$Cl, or Ph$_2$PCl. This general reaction has been used by German inorganic chemists such as H. Roesky and B. Kuhtz, *Chem. Ber.* (107) 1 (1974), R. Mews and O. Glemser, *Inorg. Chem.* (11) 2521 (1972), I. Ruppert, V. Bastian, and R. Appel, *Chem. Ber.* (108) 2329 (1975), U. Wannagat, *Angew. Chem.* (77) 626 (1965) and British inorganic chemists such as E. W. Abel and I.D. Towle J. *Organomet. Chem.* (122)253 (1976) and D. Armitage and A. Sinden *J. Inorg. Nucl. Chem.* (36) 993 (1974) to make nitrogen derivatives of the elements Be, B, Al, C, Si, Ge, Sn, Ti, P, As, Sb, Nb, Ta, S, Mo, W, Mn, Fe, Rh from complex element halides and usually the trimethylsilyl derivative of the nitrogen compound. The driving force of the reaction is the easy removal of by-product halosilane, the preferential pairing of the electropositive Si with electronegative halide, and the delocalization of the nitrogen lone pair in most reaction products.

This reaction proceeds rapidly in high yields at low temperatures. For example,

Mo(C$_6$H$_5$)(CO)$_3$Cl +

Ph$_2$C=NSiMe$_3$ (2x excess) $\xrightarrow{\text{6 hr, 70° C., MeOCH}_2\text{CH}_2\text{OMe solvent, 69\% yield}}$ -continued

K. Farmery, M. Kilner and C. Midcalf, *J. Chem. Soc. (A)* 2279 (1970);

H. H. Anderson, *J. Amer. Chem Soc.* (74) 1421 (1962);

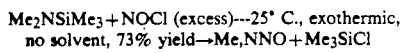

J. E. Byrne and C. R. Russ, *J. Organometal. Chem.* (22) 357 (1970); and

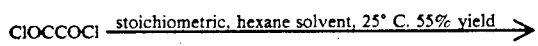

J. R. Bowser, P. J. Williams, and K. Kurz, *J. Org. Chem.* (48) 4111 (1983).

However, the general reaction does not produce interesting organosilicon compounds and thus has been of little interest to the organosilicon chemist. There have been no reports of this type of reaction being run with acrylyl chloride or methacrylyl chloride nor has there ever been mention of using a heterocyclic form of the noncarbon Group IV main group element-nitrogen linkage as part of this reaction. Certainly it has never been suggested that this type of reaction could serve as a synthetic pathway to incorporate free radical curable functionalities onto a silioxane backbone.

BRIEF SUMMARY OF THE INVENTION

The need to find a clean and simple synthetic pathway to incorporate free radical curable functionalities onto the siloxane backbone has been met by the present invention which is directed to a very general synthetic pathway to a general class of difunctional halo amide element (M) bonded nitrogen monomers and polymers of formula X—MY$_2$—R—NR'—R" where X is a halogen; M is a noncarbon Group IV main group element, R is a divalent radical, R' is a monovalent radical and R" is a group bonded to nitrogen and containing any one of at least eighteen different elements in the periodic table. The method combines the inorganic methods used to prepare various nitrogen derivatives with a cyclic noncarbon Group IV main group element-nitrogen heterocycle to yield an interesting variety of noncarbon Group IV main group compounds. The method also solves the solvent toxicity, phase separation, stability, byproduct and polymerization problems previously faced in the preparation of organosilicon derivatives.

This general class of difunctional halo amide compounds is prepared by cleaving the nitrogen-noncarbon Group IV main group element bond heterocyclic ring with a reactive halide moiety according to the following general scheme:

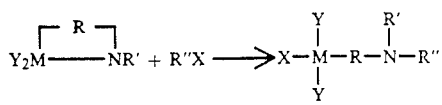

The cyclic nitrogen-noncarbon Group IV main group element compound can have any structure so long as it contains at least one cyclic noncarbon Group IV main group atom bonded to a cyclic nitrogen atom. The terminal or acyclic bonds of the cyclic noncarbon Group IV main atom are satisfied by organic radicals or by divalent, noncarbon Group IV main group-linking oxygen or nitrogen atoms. The terminal or acyclic bond of the cyclic nitrogen is satisfied by an organic radical, an inorganic radical or a hydrogen atom. The R"X compound is any compound with a halide moiety that will cleave the cyclic noncarbon Group IV main group element-nitrogen bond.

The noncarbon Group IV main group element may be silicon, germanium or tin and preferably is silicon. The noncarbon Group IV main group element-nitrogen heterocycle may be of any size and contain carbon and other noncarbon elements. Preferably the heterocyclic ring contains four to six atoms. Preferably the noncarbon Group IV main group element and nitrogen are linked by a divalent hydrocarbon radical such as an isobutylene radical The terminal valences of the noncarbon Group IV main group element are satisfied by organic radicals, alkoxy radicals, nitrogen radicals, hydrogen atoms, halogen atoms or divalent noncarbon Group IV main group element linking oxygen or nitrogen atoms. The terminal valence of the cyclic nitrogen is satisfied by such groups as an alkyl radical, an aryl radical, an inorganic radical or a hydrogen atom.

The reactive halide moiety is used to open the cyclic noncarbon Group IV main group element-nitrogen ring by cleaving the noncarbon Group IV main group element-nitrogen bond in a by-product free reaction that yields an N-aminoalkyl noncarbon Group IV main group moiety while simultaneously adding a reactive halogen on the noncarbon Group IV main group element in one step and in high yield Preferably the halide moiety is provided by a covalently bonded halide compound that yields a hydrogen halide on hydrolysis. Typically such compounds are the halides of Group II through Group VI main group elements and transition metal elements such as acyl halide, alkyl halide, phosgene, PhSO$_2$Cl, SO$_2$Cl$_2$, SOCl$_2$, S$_2$Cl$_2$, ClSO$_2$NCO, RN=SF$_2$, RN=SCl$_2$, R$_2$NSCl, ClSO$_2$NCO, PCl$_3$, OPCl$_3$, PhPOCl$_2$, (Cl$_3$P=N)$_2$SO$_2$, BCl$_3$, PhBCl$_2$, R$_2$BCl, AlCl$_3$, FeCl$_3$, BeCl$_2$, SbCl$_5$, PhN=CCl$_2$, NOCl, PR$_2$F$_3$, R$_2$AsCl, Me$_2$NSOCl, S$_3$N$_2$Cl$_2$, CF$_3$SF$_3$, (ClSO$_2$)$_2$NH, Mn(CO)$_5$Br, Mo(C$_5$H$_5$)(CO)$_3$Cl, W(C$_5$H$_5$)(CO)$_3$Cl, or Ph$_2$PCl. Preferably the halide compound is an acyl halide such as acrylyl chloride.

A cyclic nitrogen-silicon compound is given by formula I

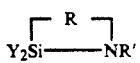

where Y denotes a divalent, silicon-linking oxygen or nitrogen atom, an organic radical, an alkoxy radical, a hydrogen atom or a halogen atom; R typically denotes a divalent hydrocarbon radical; and R' denotes a hydrocarbon radical or hydrogen atom. Preferably the cyclic ring contains four to six atoms. The formula R"X denotes a reactive halide compound where R" typically denotes a monovalent organic radical bonded to a carbonyl radical, i.e., an acyl radical, and X denotes a halide.

Advantageously the reactions and workup of the reaction of cyclic silicon-nitrogen compounds with acyl halides are straight forward with no intermediates or byproducts that require separation, filtering, washing, or other special treatment. Usually the reactions are carried out at room temperature. However, when the acyl halide is an acrylyl halide, the reaction is carried out preferably at about −10 to 10° C. to minimize byproduct formation.

Typically the cyclic compound and an acyl halide are reacted in equimolar amounts by adding the halide to the cyclic compound Any nonreactive solvent may be used. Preferably a nonaqueous solvent is used. Since solvent requirements are minimal, chlorinated solvents can be avoided thereby reducing toxicity problems The reaction is typically carried out with agitation in a dry atmosphere.

The halo functionality of the reaction product may be reacted with various reactants to produce useful derivatives. For example, the reaction of the halo noncarbon Group IV main group element group with an amide salt produces a difunctional diamide silicon compound. The reaction of the halo noncarbon Group IV main group element group with an acid salt yields an acid derivative. The reaction of the halo noncarbon Group IV main group element group with an amine gives an amino derivative. And the reaction of the halo noncarbon Group IV main group element group with a base yields a disiloxane.

The halosilicon group and certain of its derivative functionalities are capable of capping any SiOH group When the other functionality of the difunctional compound is an acrylamide, the capped entity may be cross-linked by free-radicals through the acrylamide functionality thereby producing useful products such as paper release coatings and photoresists.

Accordingly, it is an object of the present invention to provide an improved method for preparing organosilicon compounds that contain, in addition to the silicon-bonded acylamino-substituted hydrocarbon radicals of the type described in the Varaprath Pat No. 4,608,270, a second reactive halosilicon functionality. These and other objects of and advantages of the invention will become apparent from the following description and the appended claims

DETAILED DESCRIPTION OF THE PREFERRED EMBODIMENTS

The reactant heterocyclic noncarbon Group IV main group element (M)-nitrogen compound has the general formula:

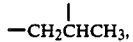

where M is a noncarbon Group IV main group element such as silicon germanium or tin. Preferably M is silicon The terminal "Y" radicals on the noncarbon Group IV main group element (M) include organic radicals and divalent, silicon-linking, oxygen and nitrogen atoms Examples of organic radicals include, but are not limited to, (1) divalent radicals such as alkylene radicals such as —CH$_2$CH$_2$—,

—CH$_2$CH$_2$CH$_2$—, —CH$_2$CH(CH$_3$)CH$_2$—, and —(CH$_2$)$_6$— and arylene radicals such as —C$_6$H$_4$—, —CH$_2$C$_6$H$_4$—, and —CH$_2$,C$_6$H$_4$CH$_2$— and halogenated derivatives thereof; and (2) monovalent radicals such as an alkyl radical such as methyl (Me), ethyl (Et), propyl, butyl (Bu), hexyl, and octyl; cycloaliphatic radicals such as cyclohexyl; aryl radicals such as phenyl (Ph), benzyl, styryl (cinnamenyl, i.e., PhCH=CH—), tolyl, and xenyl; and alkenyl radicals such as vinyl and allyl and halogenated derivatives thereof, alkoxy radicals such as methoxy and ethoxy radicals, aryloxy radicals, nitrogen radicals and hydrogen and halogen atoms.

When M is silicon and the terminal bonds of the cyclic silicon are satisfied by divalent organic radicals or by divalent, silicon-linking oxygen atoms, the heterocyclic silicon-nitrogen compound can be a silane, a siloxane, a silcarbane, or a silcarbanesiloxane. Preferably monovalent organic radicals containing no more than 6 carbon atoms, such as methyl, 3,3,3 trifluoropropyl, phenyl and vinyl radicals and, most preferably, methyl radicals are used.

The heterocycle that is to be reacted with the acyl halide can have any structure as long as it contains at least one cleavable cyclic noncarbon Group IV main group element-nitrogen bond. The divalent R radical which completes the noncarbon Group IV main group element-nitrogen heterocycle includes, but is not limited to alkylene radicals such as —CH$_2$CH$_2$—,

|
CH$_2$CHCH$_3$,

—CH$_2$CH$_2$CH$_2$—, —CH$_2$CH(CH$_3$)CH'—, and —(CH$_2$)$_6$—; oxy radicals such as —OCH(CH)$_3$CH$_2$—; and arylene radicals such as C$_6$H$_4$, —CH$_2$C$_6$H$_4$—, and —CH$_2$C$_6$H$_4$CH$_2$—. Preferably the cyclic heterocycle is a 4, 5, or 6 membered ring.

The terminal R' group on the cyclic nitrogen atom includes hydrocarbon radicals such as, but not limited to, alkyl radicals such as methyl, ethyl, propyl, butyl, hexyl, and octyl; cycloaliphatic radicals such as cyclohexyl; aryl radicals such as phenyl, benzyl, styryl (cinnamenyl), tolyl, and xenyl; and alkenyl radicals such as vinyl and allyl. The terminal R' group may also be an inorganic radical such as —SiMe$_2$CH$_2$CHMeCH$_2$Cl and a hydrogen atom.

Cyclic aminosilicon compounds and their preparation are well known in the organosilicon art. J. L. Speier, C. A. Roth and J. W. Ryan, "Synthesis of (3-Aminoalkyl) silicon Compounds" J. Org. Chem. 36, 3120 (1970). Some are commercially available. Such compounds include, but are not limited to, the following representative compounds:

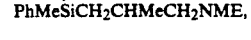

-continued

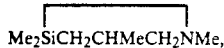

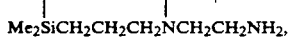

tert-BuOMeSiCH2CHMeCH2NCH2CH2NH2, and

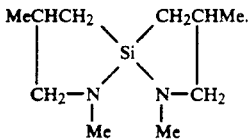

The reactive halide R"X can have any structure that provides a reactive halide that will cleave the cyclic nitrogen-silicon bond. Typically such compounds are the halides of Group II through Group VI main group elements and the transition metal elements. Suitable reactive halides are typically any primarily covalent linked halides that are hydrolyzable on exposure to water at room temperature, preferably over a period of less than about 24 hours to give hydrogen halide as a product. For example, the reactive halide can be, but is not limited to, phosphorus trihalide, alkyl or aryl sulfonyl halide, aluminum chloride, antimony pentachloride, ethylchloroformate, manganese chloropentacarbonyl, or an acyl halide. An acyl halide R"X can have any structure such as a linear, branched, or cyclic structure having aromatic, heterocyclic, olefinic or paraffinic bonding and containing one or more carbon-bonded —COX radicals, where X denotes a halogen atom. Examples of acyl halide R"X containing more than one carbon bonded —COX include succinyl chloride and suberoyl chloride. Preferably the acyl halide has the structure R"X where X denotes a halogen atom, preferably chlorine, and the acyl R" group includes but, as noted above, is not limited to a substituted or unsubstituted monovalent hydrocarbon radical bonded to a carbonyl group.

Examples of unsubstituted acyl R" group hydrocarbon radicals include, but are not limited to, monovalent radicals such as alkyl radicals such as methyl, ethyl, propyl, butyl, hexyl, and octyl; cycloaliphatic radicals such as cyclohexyl; aryl radicals such as phenyl, benzyl, styryl (cinnamenyl), tolyl, and xenyl; and alkenyl radicals such as vinyl, isopropenyl and allyl. Examples of substituted acyl R" group hydrocarbon radicals include, but are not limited to, halogenated R radicals such as —CF3 and —C6H4Cl, and other substituted radicals which are stable under the reaction conditions employed in the method of this invention such as —CH2CH2CN, —C6H4NO2 and —C(CN)=CH2. Examples of corresponding acyl halide R"X include acetyl chloride, benzoyl chloride and, most preferably, acrylyl chloride, methacrylyl chloride and cinnamoyl chloride. Other compounds of general formula R"X which provide a reactive halide are compounds otherwise corresponding thereto and having the same general properties thereof wherein the acyl group R" is replaced by other common moieties containing Group II through Group VI main group elements such as beryllium, boron, aluminum, carbon, silicon, germanium, tin, phosphorus, arsenic, antimony, niobium or sulfur of a transition metal such as tungsten, iron, rhodium, manganese, molybdenum, tantalum or titanium, e.g., where PCl3, AlCl3, FeCl3 or NOCl is used instead of an acyl halide.

The solvent can be any suitable liquid that will not react with the components of the reaction. Dry, nonaqueous solvents are used since the reactants are typically moisture sensitive. Preferably the solvent is also a solvent for the organosilicon product of the reaction. Examples of suitable solvents include, but are not limited to, hydrocarbons such as toluene, xylene, hexane, cyclohexane and hydrocarbons such as methylene chloride, chloroform, trichloroethylene and trichloroethane; and oxygenated compounds such as ethyl ether and ethyl acetate. Mixtures of two or more solvents can also be used, it only being required that the mixture, and not necessarily all of the components in the mixture, be a solvent for all the starting materials. Preferably, a nontoxic solvent such as toluene or diethyl ether is used. The amount of solvent that is used should be sufficient to dissolve the starting materials and, preferably, the halosilicon amide product as well. Except when the acyl halide is an acrylyl halide, the method of this invention can be practiced at any reasonable temperature. Advantageously this method proceeds readily at room temperature. When an acrylyl halide is used, this method should be practiced at a relatively low temperature to minimize the formation of byproducts. Accordingly, when using the method of this invention to prepare acrylyl-substituted aminosilicon compounds, the reaction should be conducted at a temperature of from about −10 to about 10° C. Higher reaction temperatures substantially reduce the yield of desired product.

The usual low shear means such as stirrers, paddles, and impellers are sufficient to maintain sufficient agitation. Agitation is maintained until the acylation reaction is finished, typically within an hour.

After the reaction is finished, the solvent can be removed from the product using conventional means such as a rotary evaporator. When acrylyl-substituted products are to be separated from the solvent, it is desirable to add a polymerization inhibitor such as sodium nitrite to the solution prior to any separating action such as distilling or fractionation.

Derivatives of the difunctional halosilicon amide are prepared by reacting the halo functionality of the product halosilicon amide with various reactants such as an alkali metal amide, an alkali metal salt of an organic acid, an alkali metal amine salt or an alkali metal hydroxide to give the corresponding diamide, acid derivative, amine derivative, or oxy dimer. Since the halosilicon amide product and its derivatives except the oxy dimer will convert any SiOH unit to acylamide functionality, they are all useful as endcapping agents. When the acyl halide is an acryl halide, the product halosilicon acrylamide and its derivatives not only serve as endcapping agents but also serve to introduce the free radical polymerizable acrylamide functionality onto the endcapped silicon unit. These encapped silicon units with a polymerizable acrylamide functionality are useful in the production of various cross-linked products including photoresists, moisture and radiation dual cure conformal coatings, coupling agents, paper release coatings, among others.

The products of this method are useful as polar silicon-containing additives for cosmetic compositions, coating compositions, textile treating compositions, and paints. The compositions are useful as comonomers with polymerizable vinyl monomers such as styrene, butadiene, methyl methacrylate, ethyl acrylate, vinyl acetate, vinyl chloride, vinylidene chloride and acrylonitrile. In particular the compounds having acrylamide radicals as a reactive component in free radical curable compositions such as radiation curable compositions used for paper, resin protective, and optical fiber coatings.

The following examples are disclosed to further teach the practice of the invention and are not intended to limit the invention as it is delineated in the claims.

EXAMPLE 1

Reaction of 1,2,2,4 tetramethyl-1-aza-2-silacyclopentane with acrylyl chloride.

A two liter three necked flask equipped with a nitrogen inlet, dropping funnel, thermometer and a magnetic stir bar was charged with 196.0 g (1.37 moles) of 1,2,2,4tetramethyl-1-aza-2-silacyclopentane and 600 ml of anhydrous diethyl ether. The mixture was stirred and was cooled externally in an ice bath. To this 123.6 g (1.37 moles) of acrylyl chloride dissolved in 400 ml of anhydrous ether was slowly added with stirring. The temperature of the reaction mixture was maintained at $5\pm1°$ C. Addition took approximately 5 hrs. The mixture was stirred overnight. Solvent was removed under reduced pressure to yield the product, N-methyl-N-[2-methyl-3-(chlorodimethylsilyl) propyl]-2-propenamide, $(ClSi(Me)_2CH_2CH(CH_3)CH_2N(CH_3)COCH=CH_2)$, in quantitative yield. The product was characterized by gas-liquid chromotography (glc), IR and NMR spectra. $^1H$ NMR (CDCl$_3$, 400 MHz): 6.5–5.5 (CH$_2$=CH), 3.25–3.0(N-CH$_2$), 2.9–2.75 (N—CH$_3$), 2.0 (CH—CH$_2$), 0.85–0.80 (CH—CH$_3$), 0.3–0.5 (SiCH$_2$), and 0.3 (Si—CH$_3$); $^{13}C$ NMR (CDCl$_3$): 166.4 and 166.3 (C=O), 127.5 (CH$_2$=CH), 127.3 (CH$_2$=CH), 57.87 and 55.7 (N—CH$_2$—), 35.8 and 34.1 (N-CH$_3$), 28.5 and 27.3 (CH$_2$—CH), 23.8 and 23.5 (—SiCH$_2$—CH), 19.8 and 19.4 (CH$_3$—CH); $^{29}Si$ (CDCl$_3$): 31.34 and 30.87. IR (neat): 1650 cm$^{-1}$(C=O) and 1620 cm$^{-1}$(C=C).

EXAMPLE 2

Reaction of 1,2,2,4 tetramethyl-1-aza-2-silacyclopentane with acetyl chloride.

A one liter three-necked flask was equipped with a thermometer, nitrogen inlet, 125 ml capacity pressure equalizing dropping funnel and a magnetic stir bar. The cyclic silazane (100.0 g; 0.6993 mmoles) dissolved in 250 g of dry ether was transferred into the flask. The flask was cooled externally using an ice bath. When the temperature of the solution reached 5 ° C., acetyl chloride (54.89 g; 0.6993 mmoles) dissolved in 50 g of dry ether was gradually added to the stirred solution. Addition took approximately one hour. After the addition was over, the mixture was stirred for another 4 hrs. The solvent was removed under reduced pressure. The product, $ClSi(Me)_2CH_2CH(CH_3)CH_2N(CH_3)COMe$, was distilled (70–80° C./0.1 mm Hg). The product was characterized by proton NMR, Carbon-13 NMR, Silicon-29 NMR, and IR. H$_1$NMR (CDCl$_3$) 3.2–3.0 (N—CH$_2$,(m)), 2.9–2.8 (N—CH$_3$), 2.0 (COCH$_3$ and CH), 1.0 (CH—CH$_3$(d)), 0.8–0.5 (SiCH$_2$); 0.3 (SiCH$_3$). $^{13}C$ NMR (CDCl$_3$): 170 (C=O), 58.3 and 54.9 (N—CH$_2$—), 36.0 and 32.7 (N-CH$_3$), 27.6 and 26.9 (CH—CH$_3$), 23.4 and 23.1 (—SiCH$_2$—CH), 21.2 and 20.9 (COCH$_3$), 19.4 and 19.0 (CH—CH$_3$), 2.0 (si—CH$_3$). $^{29}Si$ NMR (CDCl$_3$): 31.38, 30.91. IR (neat): 1655 CM$^{-1}$ (C=O).

EXAMPLE 3

Reaction of 1,2,2,4 tetramethyl-1-aza-2-silacyclopentane with methacrylyl chloride or with ethyl chloroformate.

Using the general method outlined in Example 2, $ClSi(Me)_2CH_2CH(CH_3)CH_2N(CH_3)COC(CH_3)=CH_2$ was prepared by the reaction of 1,2,2,4 tetramethyl-1-aza-2-silacyclopentane with methacrylyl chloride and $ClSi(Me)_2CH_2CH(CH_3)CH_2N(CH_3)COOEt$ was prepared by the reaction of 1,2,2,4 tetramethyl-1-aza-2-silacyclopentane with ethyl chloroformate. Removal of solvent under reduced pressure afforded the liquid product.

EXAMPLE 4

Reaction of 1,2,2,4 tetramethyl-1-aza-2-silacyclopentane with benzoyl chloride.

A 500 ml three-necked flask equipped with a thermometer, nitrogen inlet, dropping funnel and a magnetic stir bar was charged with 39.32 g (0.275 moles) of 1,2,2,4 tetramethyl-1-aza-2-silacyclopentane dissolved in 100 ml of ether. The flask was colled externally in an ice bath. Benzoyl chloride (38.64 g; 0.275 moles) dissolved in 50 ml of ether was gradually added over a period of 2 hrs to the solution of 1,2,2,4 tetramethyl-1-aza-2-silacyclopentane. The mixture was stirred for an additional 2 hrs. Solvent was removed under reduced pressure. The product, $ClSi(Me)_2CH_2CH(CH_3)CH_2N(CH_3)COPh$, was isolated and characterized by $^1H$ NMR which correlated with the expected structure.

EXAMPLE 5

Reaction of 1,2,2,4 tetramethyl-1-aza-2-silacyclopentane with benzene sulfonyl chloride A 250 ml three-necked flask was equipped with a thermometer. To the flask a solution of 10.0 g (69.9 mmoles) of 1,2,2,4 tetramethyl-1-aza-2-silacyclopentane in 40 ml of dry ether was added. The flask was cooled in an ice bath and 12.3 g (69.9 mmoles) of benzene sulfonyl chloride (C$_6$H$_5$SO$_2$Cl) dissolved in 10 ml of ether was gradually added over a period of 30 minutes. The mixture was stirred for two hrs and solvent removed under reduced pressure. The product was characterized by 200 MHz proton NMR (CDCl$_3$; tetramethylsilane (TMS)): 8.0–7.3 (m, 6.0, C$_6$H$_5$), 2.90–2.58 (m, 5.7, N—CH$_2$, N—CH$_3$), 2.0–1.9(m, 1.2, CH—CH$_2$), 1.2–0.9

(m, 4.6, CH—CH$_3$), 0.7–0.5(m, 0.96, SiCH$_2$), 0.4 (s, 5.5, Si—CH$_3$).

EXAMPLE 6

Reaction of 1,2,2,4 tetramethyl-1-aza-2-silacyclopentane with succinyl chloride.

Cyclic silazane (1,2,2,4 tetramethyl-1-aza-2-silacyclopentane, 18.45 g, 129.0 mmoles) was dissolved in 125 ml of dry ether and placed in a 250 ml three-necked flask fitted with a magnetic stir bar, nitrogen inlet, thermometer and a dropping funnel. The reaction mixture was stirred and cooled to 0 ° C. using a dry-magnetic ice/isopropanol bath. To this stirred mixture, 10.0 g (64.5 mmoles) of succinyl chloride dissolved in 35 ml of dry ether was added dropwise. After the addition of succinyl chloride was over, the mixture was stirred for an additional 1 hr. Solvent was removed under reduced pressure and the isolated product, [(ClSi(-Me)$_2$CH$_2$CH(CH$_3$)CH$_2$N(CH$_3$)),COCH$_2$]$_2$, was characterized by $^1$H HMR and IR.

EXAMPLE 7

Reaction of 1,2,2,4 tetramethyl-1-aza-2-silacyclopentane with suberoyl chloride

The reaction of 1,2,2,4 tetramethyl-1-aza-2-silacyclopentane and suberoyl chloride was carried out in a similar manner as that for the reaction with succinyl chloride in Example 6 except that an ice water bath was used instead of the dry-ice/isopropanol bath. In this case 10.0 g (69.9 mmoles) of 1,2,2,4 tetramethyl-1-aza-2-silacyclopentane and 7.38 g (35.0 mmoles) of suberoyl chloride was used.

EXAMPLE 8

Reaction of N-methyl-N-[2-methyl-3-(chlorodimethylsilyl)propyl]-2-propenamide with the sodium salt of N-methylacetamide.

Chlorosilane, i.e., 319.2 g (1.37 moles) N-methyl-N-[2-methyl-3-(chlorodimethylsilyl)propyl]-2propenamide, was placed in a dropping funnel and diluted with 200 ml of dry toluene. The chlorosilane solution was gradually added to a slurry of a sodium salt of N-methylacetamide in xylene. The reaction was slightly exothermic with the temperature increasing from about 23° to 30 ° C. The mixture was stirred overnight. Sodium chloride was removed by centrifugation and most of the solvent was removed under reduced pressure. The product N-methyl acetamide derivative was characterized by Fourier transform infrared spectroscopy (FTIR) and $^{29}$Si NMR techniques.

EXAMPLE 9

Reaction of N-methyl-N-[2-methyl-3-(chlorodimethylsilyl)propyl]-2-propenamide with sodium acetate.

Sodium acetate (1.9 g; 23.2 mmoles) was added to 5 g (21.4 mmoles) of N-methyl-N-[2-methyl-3-(chlorodimethylsilyl)propyl]-2-propenamide in 50 ml of hexane. The mixture was stirred and heated to reflux for 24 hr. The reaction mixture was allowed to cool. The salt was filtered and solvent removed to obtain the acetate derivative.

EXAMPLE 10

Preparation of disiloxane from N-methyl-N-[2-methyl-3(chlorodimethylsilyl)propyl]-2-propenamide.

To an ethereal solution of 2 g (8.5 mmoles) of N-methyl-N-[2-methyl-3-(chlorodimethylsilyl)propyl]-2-propenamide was added dilute sodium hydroxide solution. The mixture was stirred for 10 minutes, the ether layer was separated, washed with water, dried over anhydrous sodium sulfate and solvent removed to obtain the confirmed by $^1$H NMR and IR spectra.

EXAMPLE 11

Using known methods for cleaving acyclic silicon-nitrogen bonds with various complex element halides R″X where R″ is a complex element moiety (Roesky and B. Kuhtz, *Chem. Ber.* 107, 1 (1974), U. Wannagat, *Angew. Chem.* 77, 626 (1965), E. W. Abel and I. D. Towle, *J. Organomet. Chem.*, 122, 253 (1976), and D. Armitage and A. Sinden, *J. Inorg. Nucl. Chem.* 36, 993 (1974)), the following equivalent products are made by reacting the indicated equivalent complex element halides with 1,2,2,4 tetramethyl-1-aza-2-silacyclopentane:

| R″X | Reaction Products |
|---|---|
| COCl$_2$ | ClSi(Me)$_2$CH$_2$CH(CH$_3$)CH$_2$N(CH$_3$)COCl |
|  | (ClSi(Me)$_2$CH$_2$CH(CH$_3$)CH$_2$N(CH$_3$))$_2$CO |
| SO$_2$Cl$_2$ | ClSi(Me)$_2$CH$_2$CH(CH$_3$)CH$_2$N(CH$_3$)SO$_2$Cl |
| SOCl$_2$ | ClSi(Me)$_2$CH$_2$CH(CH$_3$)CH$_2$N(CH$_3$)SOCl |
| AlCl$_3$ | ClSi(Me)$_2$CH$_2$CH(CH$_3$)CH$_2$N(CH$_3$)AlCl$_2$ |
| SbCl$_5$ | ClSi(Me)$_2$CH$_2$CH(CH$_3$)CH$_2$N(CH$_3$)SbCl$_4$ |
| FeCl$_3$ | ClSi(Me)$_2$CH$_2$CH(CH$_3$)CH$_2$N(CH$_3$)FeCl$_2$ |
| BeCl$_2$ | (ClSi(Me)$_2$CH$_2$CH(CH$_3$)CH$_2$N(CH$_3$))$_2$Be |
| POCl$_3$ | ClSi(Me)$_2$CH$_2$CH(CH$_3$)CH$_2$N(CH$_3$)POCl$_2$ |
| Mn(CO)$_5$Cl | ClSi(Me)$_2$CH$_2$CH(CH$_3$)CH$_2$N(CH$_3$)Mn(CO)$_5$ |
| R′$_2$AsCl | ClSi(Me)$_2$CH$_2$CH(CH$_3$)CH$_2$N(CH$_3$)AsR′$_2$ |
| ClSO$_2$NCO | ClSi(Me)$_2$CH$_2$CH(CH$_3$)CH$_2$N(CH$_3$)SO$_2$NCO |
| alkyl-X | ClSi(Me)$_2$CH$_2$CH(CH$_3$)CH$_2$N(CH$_3$)alkyl |
| R′N=SF$_2$ | (ClSi(Me)$_2$CH$_2$CH(CH$_3$)CH$_2$N(CH$_3$))$_2$S=NR′ |
| ClSO$_2$NCO | ClSi(Me)$_2$CH$_2$CH(CH$_3$)CH$_2$N(CH$_3$)SO$_2$NCO |
| Cl$_3$P=NSO$_2$N=PCl$_3$ | ClSi(Me)$_2$CH$_2$CH(CH$_3$)CH$_2$N(CH$_3$)Cl$_2$P=NSO$_2$N=PCl$_3$ |
| R′$_2$NSCl | ClSi(Me)$_2$CH$_2$CH(CH$_3$)CH$_2$N(CH$_3$)SNR′$_2$ |
| PhPOCl$_2$ | (ClSi(Me)$_2$CH$_2$CH(CH$_3$)CH$_2$N(CH$_3$))$_2$POPh |
| PhBCl$_2$ | (ClSi(Me)$_2$CH$_2$CH(CH$_3$)CH$_2$N(CH$_3$))$_2$BPh |
| PhN=CCl$_2$ | (ClSi(Me)$_2$CH$_2$CH(CH$_3$)CH$_2$N(CH$_3$))$_2$C=NPh |
| PR′$_2$F$_3$ | ClSi(Me)$_2$CH$_2$CH(CH$_3$)CH$_2$N(CH$_3$)PR′$_2$F$_2$ |
| R′$_2$AsCl | ClSi(Me)$_2$CH$_2$CH(CH$_3$)CH$_2$N(CH$_3$)AsR′$_2$ |
| S$_3$N$_2$Cl$_2$ | ClSi(Me)$_2$CH$_2$CH(CH$_3$)CH$_2$N(CH$_3$)ClN$_2$S$_3$ |
| Me$_2$NSOCl | ClSi(Me)$_2$CH$_2$CH(CH$_3$)CH$_2$N(CH$_3$)OSNMe$_2$ |

-continued

| R"X | Reaction Products |
|---|---|
| (ClSO$_2$)$_2$NH | (ClSi(Me)$_2$CH$_2$CH(CH$_3$)CH$_2$N(CH$_3$)SO$_2$)$_2$NH |
| Ph$_2$PCl | ClSi(Me)$_2$CH$_2$CH(CH$_3$)CH$_2$N(CH$_3$)PPh$_2$ |
| W(C$_5$H$_5$)(CO)$_3$Cl | ClSi(Me)$_2$CH$_2$CH(CH$_3$)CH$_2$N(CH$_3$)W(CO)$_2$(C$_5$H$_5$) |
| Mo(C$_5$H$_5$)(CO)$_3$Cl | ClSi(Me)$_2$CH$_2$CH(CH$_3$)CH$_2$N(CH$_3$)Mo(CO)$_2$(C$_5$H$_5$) |
| PCl$_3$ | ClSi(Me)$_2$CH$_2$CH(CH$_3$)CH$_2$N(CH$_3$)PCl$_2$ |

What is claimed is:

1. A method for preparing a derivative of a difunctional halo noncarbon Group IV main group element amide comprising: reacting the halo functionality of said difunctional halo noncarbon Group IV main group element amide with a reactant selected from the group consisting of an alkali metal amide, an alkali metal salt of an organic acid, an amine, an alkali metal amine salt, and an alkali metal hydroxide; said difunctional halo noncarbon Group IV main group element amide having been prepared by a process comprising cleaving a noncarbon Group IV main group element-nitrogen bond in a heterocyclic ring with a reactive halide moiety.

2. A method according to claim 1 wherein said noncarbon Group IV main group element is sleeted from the group consisting of silicon, germanium, and tin.

3. A method according to claim 2 wherein said noncarbon Group IV main group element is silicon.

4. A method according to claim 1 wherein said heterocyclic ring contains four to six atoms.

5. A method according to claim 1 with said heterocyclic ring comprising a divalent hydrocarbon radical bonded to said nitrogen and to said noncarbon Group IV main group element.

6. A method according to claim 5 wherein said divalent hydrocarbon radical is an isobutylene radical.

7. A method according to claim 1 wherein the terminal valences of the noncarbon Group IV main group element are satisfied by radicals selected from the group consisting of organic radicals, alkoxy radicals, nitrogen radicals, hydrogen atoms, halogen atoms and divalent, noncarbon Group IV main group element-linking, oxygen and nitrogen atoms.

8. A method according to claim 1 wherein the terminal valence of said nitrogen is satisfied by a radical selected from the group consisting of alkyl radicals, aryl radicals, inorganic radicals and hydrogen atoms.

9. A method according to claim 1 wherein said noncarbon Group IV main group element amide has the formula XY$_2$MRNR'R" wherein Y denotes an organic radical, an alkoxy radical, a nitrogen radical, a hydrogen atom, a halogen atom or a divalent, silicon linking oxygen or nitrogen atom;

R denotes a divalent radical;

R' denotes a hydrocarbon radical, an inorganic radical or a hydrogen atom;

R" denotes an acyl radical;

X denotes a halide; and

M denotes the noncarbon Group IV main group element.

10. A method according to claim 9 wherein M is silicon, X is chlorine and R is a hydrocarbon radical.

11. A method according to claim 10 wherein R" is an acrylyl radical.

12. A method according to claim 11 wherein R is isobutylene, Y is methyl and R' is methyl.

13. A method according to claim 12 wherein the reactant is the sodium salt of N-methylacetamide.

14. A method according to claim 12 wherein the reactant is sodium acetate.

15. A method according to claim 12 wherein the reactant is sodium hydroxide.

* * * * *